United States Patent [19]

Beck et al.

[11] Patent Number: 5,099,051
[45] Date of Patent: Mar. 24, 1992

[54] SILOXANYL-PHOSPHATE MIXTURE AND ITS USE IN STABILIZING METAL SILANOLATES IN SILOXANE POLYMERS

[75] Inventors: James A. Beck; Peter Lamont, both of Midland, Mich.

[73] Assignee: Dow Corning Corporation, Midland, Mich.

[21] Appl. No.: 745,823

[22] Filed: Aug. 16, 1991

[51] Int. Cl.$^5$ .................................................. C07F 7/08
[52] U.S. Cl. ............................... 556/401; 556/405; 528/14; 528/23
[58] Field of Search .................. 556/405, 401; 528/14, 528/23

[56] References Cited

U.S. PATENT DOCUMENTS 4,125,551 11/1978 Peterson ..................... 260/448.2 E
4,177,200 12/1979 Razzaro et al. .............. 260/448.2 N
5,041,586 8/1991 Beck et al. ......................... 556/405

FOREIGN PATENT DOCUMENTS 173332 5/1976 Czechoslovakia.

Primary Examiner—Paul F. Shaver
Attorney, Agent, or Firm—Roger H. Borrousch

[57] ABSTRACT

Siloxanyl-phosphate mixtures are prepared by reacting cyclopolydimethylsiloxane and a silylphosphate mixture. The siloxanyl-phosphate mixture is a mixture of 5 to 30 weight percent of a monosiloxanyl-phosphate of the formula

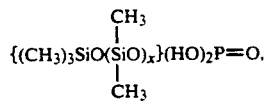

70 to 85 weight percent of a disiloxanyl-phosphate of the formula

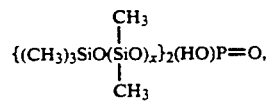

2 to 11 weight percent of a trisiloxanyl-phosphate of the formula

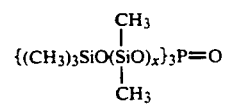

wherein x has an average value of from 3 to 30.

These siloxanyl-phosphate mixtures are useful in stabilizing basic polymerization catalyst such as potassium hydroxide or potassium silanolate and can either be used effectively per se or in combination with carbon dioxide.

5 Claims, 1 Drawing Sheet

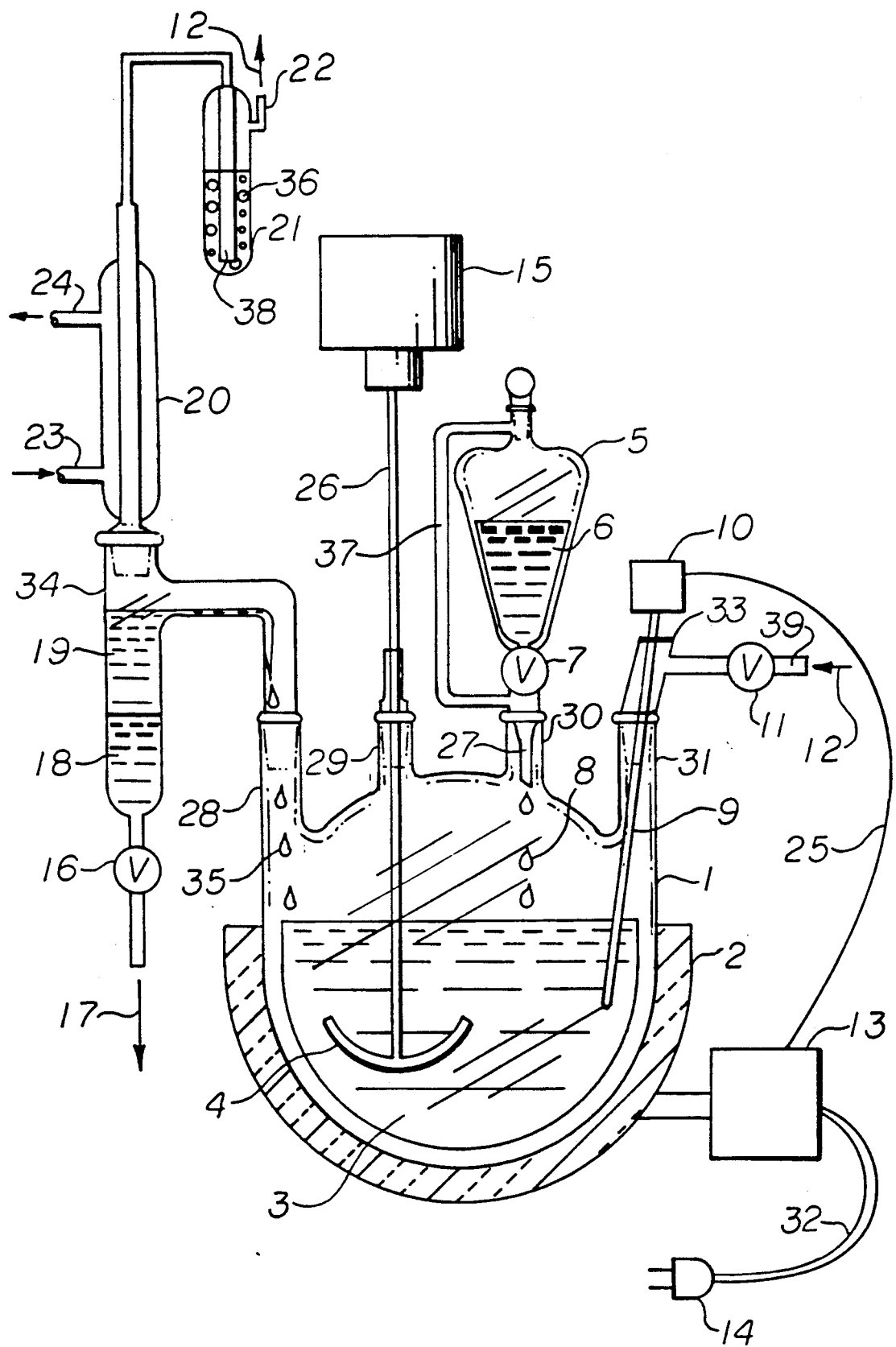

SILOXANYL-PHOSPHATE MIXTURE AND ITS USE IN STABILIZING METAL SILANOLATES IN SILOXANE POLYMERS

BACKGROUND OF THE INVENTION

1. Field of the Invention

This invention relates to siloxanyl-phosphates and their use in stabilizing alkali metals and alkaline earth metals in polyorganosiloxanes.

2. Background Information

Polydiorganosiloxanes are used in many products, such as various kinds of silicone rubbers and fluids. Many of the products require property stability under high temperature exposure to function properly in their intended utility. Because the polydiorganosiloxanes are most often made by a polymerization process involving strong base equilibration of linear polydiorganosiloxane hydrolyzates or cyclic polydiorganosiloxanes and because this equilibration proceeds via a silicon-oxygen-silicon bond breakage and reformation, the basic polymerization catalyst used must be rendered ineffective if it remains in the final product. The amount of the basic compound is very small and difficult to remove at reasonable cost, so techniques have been developed to reduce the catalyst's harmful effects. The methods of neutralizing the catalyst's activity have varied effectiveness and each method seems to have one or more disadvantages.

Polydiorganosiloxane can be prepared by the well known process of converting low molecular weight linear polydiorganosiloxanes and cyclic polydiorganosiloxanes by heating above 100° C. in the presence of potassium hydroxide or potassium silanolate. Other known alkali metal catalysts for this kind of polymerization. are sodium hydroxide, cesium hydroxide, lithium hydroxide, and their corresponding silanolates or siloxanates. In the case of the cyclic polydiorganosiloxane polymerization, a ring opening reaction takes place with the formation of linear polymers. Most often, such as in the case of polydimethylsiloxane the resulting product of the equilibration reaction is about 85% linear polymer and 15% cyclic polydimethylsiloxanes. The presence of the cyclic siloxanes in products is undesirable because they are of low molecular weight and have a sufficiently high vapor pressure to cause problems during use, such as problems in closed or semiclosed conditions where electrical or electronic equipment is in close proximity with silicone rubber and therefore, these cyclic siloxanes should be removed. The most convenient method of removing these cyclic siloxanes is by heating under reduced pressure, however, if the basic catalyst's activity is not hindered, the distillation process will continuously generate cyclic siloxanes; as they are removed from the linear polydiorganosiloxane product, more will be formed because of the reaction's potential to go to equilibrium. Therefore, it is important even in the preparation of the linear polydiorganosiloxanes to stabilize the basic catalyst. Various methods of stabilizing this basic catalyst have been used in the past. Terms, such as neutralizing the catalyst or killing the catalyst have been used in the art with various meanings. The inventors in this application use the term stabilizing the catalyst or stabilization of the catalyst to mean reducing the deleterious activity of metal ions resulting from polymerization reactions, thereby making them ineffective, for the most part, to cause Si—O—Si bond rearrangement and cyclic formation.

One method of neutralizing the basic catalyst is the use of various types of acids. One difficulty with strong acids such as hydrochloric acid or sulfuric acid is that the amount of the acid used must be very carefully controlled because either excess base or excess acid will be detrimental to the final linear polydiorganosiloxanes stability. Both acids and bases are known equilibration catalysts, thus both produce similar results if left in the product. It is known that excess acid will cause degradation of the product similar to the degradation resulting from base such as alkali metal hydroxides. It is difficult to get the base completely neutral using a strong acid and would be very expensive and time consuming. Weak acids have also been used, such as acetic acid, but these acids have a similar problem.

Phosphoric acid, because it is a buffering kind of acid, has the ability to overcome the strong acid problem of neutralizing the basic catalysts used in the preparation of linear polydiorganosiloxane through an equilibration reaction. However, phosphoric acid is not soluble in the linear polydiorganosiloxane or in the cyclic polydiorganosiloxanes and to be an effective catalyst stabilizer it needs to be soluble so that it can get to the alkali metal ions which are often located, when equilibrium is reached, on the terminal silicon atoms of the polydiorganosiloxane product as Si—O—M where M is an alkali metal atom. Solvents are not useful because solvents for the phosphoric acid are not solvents for the siloxanes and solvents for the siloxanes are not solvents for the phosphoric acid. To overcome the difficulty with the insolubility of the phosphoric acid, Razzano et al in U.S. Pat. No. 4,177,200, issued Dec. 4, 1979, found a soluble form of phosphoric acid which could be used to neutralize siloxane mixtures containing alkali metal hydroxides. Razzano et al found that the known silyl phosphates made by reacting phosphoric acid and octylmethylcyclictetrasiloxane and a small amount of hexamethyldisiloxane could be used to neutralize alkali metal hydroxide in siloxanes. However, Razzano et al reported two difficulties with this silyl phosphate. The viscosity of the silyl phosphate was too high, greater than 500 centipoise at 25° C. and this made it difficult to blend with the siloxane equilibration reaction mixture. The other difficulty reported was that the phosphoric acid content of the silyl phosphate could only achieve a maximum of 10 to 15% by weight.

Razzano et al describe a silylphosphate made by reacting a siloxane selected from the class of siloxanes of the formula $(R_3Si)_2O$ and siloxanes of the formula $R_3Si(R_2SiO)_xOSiR_3$ with phosphorous oxyhalogens $POCl_3$ or $POBr_3$ where R is a hydrocarbyl radical free of aliphatic unsaturation and x varies from 1 to 20. Razzano et al also describe a less preferred method for preparing silylphosphates by reacting phosphoric acid with linear siloxanes at temperaturea above 150° C. The advantage given for using phosphoric acid in this case is that less of the linear siloxanes are used up in the formation of the silylphosphates. According to Razzano et al, the reaction of phosphoric acid with the siloxanes is difficult and does not take place readily unless temperatures 150° C. to 200° C. are reached. Razzano et al, in a solvent, reacts 1 mole of phosphoric acid with 1.5 moles or more of the siloxane, preferably from 1.5 to 6 moles of the linear siloxanes per mole of phosphoric acid. The by-produced water is distilled off until the reaction is completed taking 1 to 7 hours. The silylphosphate produced are $(R_3SiO)_3P=O$ and $\{R_3SiO(R_2SiO)_x\}_3P=O$ where R and x are defined above. Razzano et al report that because the reaction is carried out with more difficulty and may not proceed to completion there may be some amounts of monosilyl and disilyl substituted phosphate reaction products and the phosphoric acid will be left with one or two hydroxyl groups. The monosilyl and disilyl substituted reaction products may constitute as much as 10% by weight, preferably not more than 5% by weight of the total reaction mixture. The silyl phosphate reaction product consisting mostly of trisilyl substituted phosphates is used to neutralize the equilibration siloxane reaction mixtures having alkali metal hydroxide.

An improved method for preparing silylphosphates from phosphoric acid and linear low molecular weight polysiloxane is described by Petersen in U.S. Pat. No. 4,125,551, issued Nov. 14, 1978. The method taught by Petersen comprises reacting 1 to 30 parts by weight of phosphoric acid with 100 parts by weight of polysiloxane of the formula $R(R_2SiO)_wSiR_3$ where R is a monovalent hydrocarbon radical and w is from 1 to 100 in the presence of 1.2 to 180% by weight of the total composition of a silyl phosphate catalyst in which the phosphoric acid equivalent in the reaction mixture is from 0.36 to 1.80%.

Petersen teaches that the reaction is carried out by placing 5 to 25% of the total phosphoric acid in contact with the polysiloxane and the silyl phosphate catalyst, the mixture is heated and the remaining phosphoric acid is added. The reaction began at 150° C. in most cases and varied upwardly during the reaction period until the final temperature of 175° C. to 196° C. was reached. Peterson found that in all cases where no silyl phosphate catalyst was used in the reaction mixture, the reaction did not initiate for a substantial period of time and then the reaction was violent. Petersen describes the product of the method, as a polymer not having a single composition, but a statistical distribution of a variety of structures and molecular weights about a center point.

Peterson also describes a method of making the silylphosphates by reacting phosphoric acid, a polysiloxane, diorganocyclosiloxane and silyl phosphate as a catalyst. This method, according to Petersen, is no different than the method when no diorganocyclosiloxane is used to produce the trisilyl substituted phosphates.

The process described by Razzano et al which uses $POCl_3$ or $POBr_3$ to make silylphosphate makes trisilyl phosphates and has the disadvantage of by-producing large amounts of triorganochlorosilane or triorganobromosilane. The method described by Razzano et al which combines phosphoric acid and siloxane to make silylphosphate is violent as described by Petersen who describes the use of a silylphosphate catalyst to make silylphosphate from phosphoric acid and siloxane.

Czechoslovakian Patent No. 173,332, published May 28, 1976, to Dvorak et al teach that making tris(trimethylsilyl)phosphate in high yields from phosphoric acid and hexamethyldisiloxane requires high pressure and high temperature. For example, the reaction is carried out at a pressure of 1 to 10 atmospheres at a temperature of 200° C. for three hours.

In our copending application Ser. No. 07/622,051, filed Nov. 29, 1990 now U.S. Pat. No. 5,041,586, we described a silylphosphate mixture consisting essentially of 10 to 30 weight percent of a monosilyl phosphate of the formula $\{(CH_3)_3SiO\}(HO)_2P=O,$ 70 to 85 weight percent of a disilyl phosphate of the formula $\{(CH_3)_3SiO\}_2(HO)P=O,$ and 2 to 7 weight percent of a trisilyl phosphate of the formula $\{(CH_3)_3SiO\}_3P=O.$ Our copending application Ser. No. 07/622,051 is hereby incorporated by reference to show the silylphosphate mixture.

Our copending application Ser. No. 07/622,051 also describes a method of making the mixture of silylphosphates comprising heating hexamethyldisiloxane to reflux in a closed container equipped with a condenser means, a water trapping means, and a controllable addition means, the hexamethyldisiloxane at reflux existing with a liquid phase and a vapor phase in equilibrium in the closed container, slowly adding phosphoric acid to the hexamethyldisiloxane liquid phase with the controllable addition means while maintaining reflux, the phosphoric acid addition is continued until 40 to 65 parts by weight are added per 100 parts by weight of hexamethyldisiloxane, collecting by-produced water with the water trapping means and removing the collected water at a rate sufficient to keep the water from returning to the liquid phase hexamethyldisiloxane, allowing the temperature of the liquid phase hexamethyldisiloxane to increase to a temperature in the range of 150° C. to 190° C. after the addition of the phosphoric acid is completed, recovering a mixture of silylphosphates. Our copending application Ser. No. 07/622,051 is hereby incorporated by reference to show the preparation of the silylphosphate mixture.

Our copending application also describes using the above described mixture of silylphosphates to stabilize the metal ions in a method of making polydiorganosiloxanes using basic compound having a metal ion comprising combining cyclic polydiorganosiloxanes and the basic compound and heating to polymerize the cyclic polydiorganosiloxane, thereafter stabilizing the metal ion in the resulting polydiorganosiloxane using the mixture of silylphosphates. The above method of stabilizing the metal ion in polydiorganosiloxanes prepared by the polymerization of cyclic polydiorganosiloxanes, can also be a combination of carbon dioxide gas and the mixture of silylphosphate described above.

These silylphosphate mixtures were developed for stabilizing the basic catalyst used in the preparation of linear polydiorganosiloxanes without the problems associated with its preparation. "Stabilizing" means making the catalyst ineffective as an Si—O—Si bond rearrangement catalyst in a practical sense, i.e. the ability of the metal ion of the catalyst to rearrange bonds is reduced to a level which produces very small amounts of cyclics when the polydiorganosiloxane is heated. This silylphosphate which is a mixture containing very little tris(trimethylsilyl) phosphate and which is prepared by a method which does not react violently, does not require a silylphosphate catalyst to produce a silylphosphate smoothly, and does not require the use of high pressure and an autoclave to produce it.

SUMMARY OF THE INVENTION

In an effort to develop the use of the silylphosphate mixture into commercially acceptable processes, the applicants discovered the siloxanyl-phosphate mixture of this invention.

This invention also relates to a mixture of siloxanyl-phosphates consisting essentially of 5 to 30 weight percent of a monosiloxanyl-phosphate of the formula $$\{(CH_3)_3SiO(\underset{\underset{CH_3}{|}}{\overset{\overset{CH_3}{|}}{Si}}O)_x\}(HO)_2P=O,$$

70 to 85 weight percent of a disiloxanyl-phosphate of the formula $$\{(CH_3)_3SiO(\underset{\underset{CH_3}{|}}{\overset{\overset{CH_3}{|}}{Si}}O)_x\}_2(HO)P=O,$$

and 2 to 11 weight percent of a trisiloxanyl-phosphate of the formula $$\{(CH_3)_3SiO(\underset{\underset{CH_3}{|}}{\overset{\overset{CH_3}{|}}{Si}}O)_x\}_3P=O$$

wherein x has an average value of from 3 to 30.

This invention also relates to a method of making siloxanyl-phosphate mixture consisting essentially of 5 to 30 weight percent of a monosiloxanyl-phosphate of the formula $$\{(CH_3)_3SiO(\underset{\underset{CH_3}{|}}{\overset{\overset{CH_3}{|}}{Si}}O)_x\}(HO)_2P=O,$$

70 to 85 weight percent of a disiloxanyl-phosphate of the formula $$\{(CH_3)_3SiO(\underset{\underset{CH_3}{|}}{\overset{\overset{CH_3}{|}}{Si}}O)_x\}_2(HO)P=O,$$

and 2 to 11 weight percent of a trisiloxanyl-phosphate of the formula $$\{(CH_3)_3SiO(\underset{\underset{CH_3}{|}}{\overset{\overset{CH_3}{|}}{Si}}O)_x\}_3P=O$$

wherein x has an average value of from 3 to 30 comprising mixing cyclopolydimethylsiloxanes having an average of from 3 to 7 dimethylsiloxane units per molecule with a silylphosphate mixture consisting essentially of 10 to 30 weight percent of a monosilyl phosphate of the formula $$\{(CH_3)_3SiO\}(HO)_2P=O,$$

70 to 85 weight percent of a disilyl phosphate of the formula $$\{(CH_3)_3SiO\}_2(HO)P=O,$$

and 2 to 7 weight percent of a trisilyl phosphate of the formula $$\{(CH_3)_3SiO\}_3P=O$$

to form a cyclopolydimethylsiloxane-silylphosphate mixture and reacting the cyclopolydimethylsiloxane-silylphosphate mixture for a time and at a temperature to produce a siloxanyl-phosphate mixture.

Another embodiment of this invention is using the above described mixture of siloxanyl-phosphates to stabilize the metal ions in polydiorganosiloxanes made by a basic compound having a metal ion comprising combining cyclic polydiorganosiloxanes and the basic compound and heating to polymerize the cyclic polydiorganosiloxane, thereafter stabilizing the metal ion in the resulting polydiorganosiloxane using the mixture of siloxanyl-phosphates.

Another embodiment of this invention is using, in the above method of stabilizing the metal ion in polydiorganosiloxanes made by the polymerization of cyclic polydiorganosiloxanes, a combination of carbon dioxide gas and the mixture of siloxanyl-phosphate mixture described above.

BRIEF DESCRIPTION OF THE DRAWING

The FIGURE contains a schematic cross section of the apparatus during the manufacture of silylphosphate using phosphoric acid and hexamethyldisiloxane, as described in copending application Ser. No. 07/622,051.

LIST OF REFERENCE NUMBERS WITH DEFINITIONS

1 ... 4-necked round bottom flask
2 ... heating mantle
3 ... liquid hexamethyldisiloxane
4 ... agitator
5 ... addition flask with pressure equalizer
6 ... phosphoric acid
7 ... addition flow control valve
8 ... phosphoric acid drops dropping into liquid hexamethyldisiloxane
9 ... thermometer
10 ... temperature controller-transmitter
11 ... inert gas flow control valve
12 ... inert gas flow direction
13 ... electrical switch with voltage adjustment
14 ... electrical connector to electrical power source
15 ... power source for driving agitator 4
16 ... drain valve
17 ... discard water from drain valve 16
18 ... water
19 ... liquid hexamethyldisiloxane from vapor condenser 20
20 ... vapor condenser
21 ... inert gas bubbler
22 ... inert gas outlet tube
23 ... cooling water inlet
24 ... cooling water outlet
25 ... electrical control wire
26 ... shaft connecting agitator 4 and power source 15
27 ... phosphoric acid delivery orifice
28 ... flask neck 29 ... flask neck
30 ... flask neck
31 ... flask neck
32 ... electrical cord
33 ... connecting tube
34 ... Dean-Stark trap receiver
35 ... liquid hexamethyldisiloxane flowing back into 4-necked round bottom flask 1
36 ... inert gas bubbles
37 ... pressure equalizer line
38 ... tube

DESCRIPTION OF THE PREFERRED EMBODIMENTS

The siloxanyl-phosphate mixture of the present invention is prepared by mixing cyclopolydimethylsiloxanes having an average of from 3 to 7 dimethylsiloxane units per molecule with a silylphosphate mixture and reacting it until a siloxanyl-phosphate mixture is obtained. This siloxanyl-phosphate mixture can be used at any point, but for consistency in stabilization, it is preferred to use the siloxanyl-phosphate formed when equilibrium is reached which may take at least one day at room temperature to less than one hour at 200° C. where the silylphosphate mixture consists essentially of 10 to 30 weight percent of a monosilyl phosphate of the formula

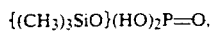

70 to 85 weight percent of a disilyl phosphate of the formula

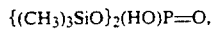

and 2 to 7 weight percent of a trisilyl phosphate of the formula

The siloxanyl-phosphate mixtures of this invention are made by mixing cyclopolydimethylsiloxanes with the silylphosphate mixture at room temperature and after about one day at room temperature, the reacting mixture will contain some siloxanyl-phosphate mixture as defined by this invention. The reaction mixture reaches equilibrium and forms a storage stable product as observed by a stable viscosity. The viscosity continually increases until equilibrium is reached and then levels off when the storage stable siloxanyl-phosphate mixture is obtained. The resulting mixture of siloxanyl-phosphates is essentially the silylphosphate species with dimethylsiloxane units inserted between the trimethylsiloxy unit and the phosphorus atom. The number of dimethylsiloxane units is from 3 to 30. The length of time for the formation of the siloxanylphosphate mixture to form varies depending on the temperature at which the reaction is carried out and the amount of silylphosphate mixture present. Higher concentrations of silylphosphate in the reacting mixture will reach equilibrium faster than lower concentrations of silylphosphate in the reacting mixture, other conditions being equal. For example, siloxanyl-phosphate usually starts forming in about one day at room temperature and may take several days to reach equilibrium, but may be taken to equilibrium in less than one hour at 200° C.

The siloxanyl-phosphate mixture of this invention can be used to stabilize metal ions in polydiorganosiloxanes made by using a basic compound having a metal ion to polymerize cyclic polydiorganosiloxanes. A combination of cyclopolydiorganosiloxane and basic compound having a metal ion is heated to polymerize the siloxane. After the polymerization has proceeded as desired, the catalytic activity of the basic compound's metal ion is stabilized by the addition of the siloxanyl-phosphate mixture. The siloxanyl-phosphate mixtures of the present invention are particularly useful for the preparation of polydiorganosiloxanes which have reactive end groups, such as vinyl or hydroxyl. Because the silylphosphate mixture of copending application Ser. No. 07/622,051 introduces trimethylsiloxy units, the end group reactivity may be reduced. Trimethylsiloxy units are unreactive groups and when they replace the vinyl or hydroxyl groups at the end of a polydiorganosiloxane, the reactivity of the resulting polymer is reduced. The siloxanyl-phosphate mixtures of the present invention, on an equal weight basis, introduce less trimethylsiloxy units. The amount of phosphorus atom can be regulated better because the weight amount of siloxanylphosphate mixture used to stabilize the metal ion is larger and can be measured more accurately.

The silylphosphate mixture, used in the preparation of the siloxanyl-phosphate mixture of this invention, can be made by the method described in copending application Ser. No. 07/622,071. These silylphosphate mixtures can be made by placing liquid hexamethyldisiloxane 3 in a reaction vessel, such as round bottom flask 1, equipped with temperature observation means (thermometer 9), an addition means, such as addition flask 6, agitator 4, and vapor condenser 20. The liquid hexamethyldisiloxane 3 is heated to reflux, about 100° C. When the hexamethyldisiloxane 3 is at reflux, the phosphoric acid 6 is added dropwise, drops 8. The phosphoric acid 6 can be syrupy phosphoric acid, i.e. 85 weight percent phosphoric acid and 15 weight percent water. As soon as the first drops 8 of phosphoric acid are added, water 18 begins to collect in the Dean-Stark trap 34. The reflux is maintained through an interacting combination of thermometer 9, temperature controller 10, connecting wire 25, electrical switch with voltage adjustment 13, and heating mantle 2. The amount of heating is controlled through this arrangement to maintain the reflux at a constant rate. The addition of phosphoric acid 6 will vary depending upon the amounts involved. The phosphoric acid is added at a rate so that the reflux rate is maintained. During the addition of phosphoric acid 6, the liquid hexamethyldisiloxane is stirred with agitator 4. The amount of agitation is not critical but should be sufficient to stir the liquid hexamethyldisiloxane 3 and keep the phosphoric acid from settling to the bottom of flask 1. The hexamethyldisiloxane vapor and the water vapor, either from the phosphoric acid-water mixture or by-produced from reaction of phosphoric acid with hexamethyldisiloxane, condenses in vapor condenser 20, the liquefied hexamethyldisiloxane and water fall into the Dean-Stark trap and separate into liquid hexamethyldisiloxane 19 which flows back into the round bottom flask 1, and water 18 which can be withdrawn at appropriate intervals so that it does not flow back into the liquid hexamethyldisiloxane in flask 1. An inert gas can be introduced, see direction of inert gas 12, through connecting tube 33 with the flow being controlled by valve 11. The inert gas can be dry nitrogen. Prior to the start of the addition of phosphoric acid, the Dean-Stark trap is preferably filled with hexamethyldisiloxane so that the amount of liquid hexamethyldisiloxane in flask 1 remains approximately constant throughout the reaction time.

Phosphoric acid is added slowly so as to maintain the reflux without loosing control, i.e. the temperature is maintained about 100° C. The amount of phosphoric acid added is sufficient to preferably provide from 40 to 65 parts by weight per 100 parts by weight of hexamethyldisiloxane. After the addition of the phosphoric acid is completed, the temperature of the reaction mixture, the material in flask 1, is allowed to increase to a temperature of from about 150° C. to 190° C., preferably about 165° C. During the period of time when the temperature of the reaction mixture is increasing to a temperature of from 150° C. to 190° C., the unreacted hexamethyldisiloxane is preferably removed. This can be done through the Dean-Stark trap 34 via valve 16. After the unreacted hexamethyldisiloxane is removed, the residue remaining in flask 1 is cooled and if it is to be stored for use at a later time, it is packaged in a moisture tight package. The mixture of silylphosphates is susceptible to degradation upon exposure to moisture and thus should be stored in a container which will not allow the ingress of moisture. The siloxanylphosphates of the present invention are also susceptible to moisture and need to be stored in a moisture tight container.

The method of preparing the silylphosphate mixture proceeds smoothly, does not require the addition of silylphosphate catalyst, and does not need high pressure or high temperatures. The product is a mixture of silylphosphates which contain less trimethylsiloxy groups which are considered contaminates in linear polydiorganosiloxanes. For example, when polydiorganosiloxanes are stabilized with the mixture of silylphosphates, the amount on triorganosiloxy units introduced is less than when the tris(trimethylsilyl) phosphate of the prior art is used. Triorganosiloxy groups can introduce such groups into the product being stabilized and thus lower amounts of trimethylsilyl groups are desirable.

The mixture of siloxanyl-phosphates is useful as a stabilizing agent for metal ions. Polydiorganosiloxane can be made by polymerizing cyclic polydiorganosiloxanes usually having on the average from 3 to 6 diorganosiloxane units per molecule with basic compounds such as metal hydroxides, namely potassium hydroxide, sodium hydroxide, lithium hydroxide, cesium hydroxide, calcium hydroxide, and magnesium hydroxide or metal silanolates derived from the same metals, preferably potassium hydroxide or potassium silanolate. This polymerization is an equilibrium reaction and the end product contains a quantity of cyclic polydiorganosiloxanes which, for most purposes, are removed. Removal of these cyclics from the product is usually done by stripping operations under reduced pressure at elevated temperature. Under such conditions cyclics would form as soon as some are removed, because an equilibrium is trying to be maintained and new cyclics are formed by the degradation of the linear polydiorganosiloxane product via Si—O—Si bond rearrangement. To overcome this problem, the metal ion, such as the potassium ion, is made ineffective, such as by stabilizing it. The siloxanyl-phosphate mixtures of this invention is a very effective metal ion stabilizer. The cyclics can be removed from the polymerization product with only very small amounts of new cyclic formation and in some cases without the formation of new cyclics. The polydiorganosiloxane product is therefore stable and the metal ion is essentially ineffective to cause degradation of the polymer chain. The amount of the mixture of siloxanyl-phosphates useful for stabilizing the metal ions in an equilibrium polydiorganosiloxane product is preferably varied to provide at least one phosphorus atom per three metal ions. Preferred amounts are from one phosphorous atom to two metal ions up to four phosphorous atoms to three metal ions. Most preferred amounts are at least one phosphorus atom per 1.5 metal ions. Because the siloxanyl-phosphate mixture allows more accurate measurement of the amount of phosphorus atom in the mixture, the stabilizing amount of phosphorus atom can be more easily adjusted to a desired ratio.

A very effective metal ion stabilization agent is a combination of carbon dioxide gas and the mixture of siloxanyl-phosphates. This combination is effective because the carbon dioxide gas rapidly stabilizes the metal ions and this method is not quite as good as desired. The addition of the siloxanyl-phosphate mixture to the carbon dioxide gas stabilizers polydiorganosiloxane forms a very stable product. The siloxanyl-phosphate mixture is somewhat slower to stabilize the metal ions of a polydiorganosiloxane product when compared to the time for the carbon dioxide gas to stabilize the metal ions of a polydiorganosiloxane.

The following examples are presented for illustrative purposes and should not be construed as limiting this invention which is properly delineated in the claims. In the following examples, "part" or "parts" are "part by weight" and "parts by weight" respectively, viscosities are at 25° C. unless otherwise specified, and Me is methyl radical.

EXAMPLE 1

A siloxanyl-phosphate mixture was prepared by first making a silylphosphate mixture.

The silylphosphate mixture was prepared in an apparatus as described by the drawing by placing 1710 grams of hexamethyldisiloxane in flask 1 with the Dean-Stark trap 34 filed with hexamethyldisiloxane. Flask 1 was heated to start the hexamethyldisiloxane to reflux, about 100° C., then syrupy phosphoric acid was added dropwise from addition flask 5 through delivery orifice 27 at a rate of about 1.25 ml per minute. Water began collecting in the Dean-Stark trap immediately and within 2 hours, 45 grams had collected and the temperature of the liquid hexamethyldisiloxane was 92° C. After 4 hours and 15 minutes, the temperature of the liquid hexamethyldisiloxane in flask 1 was 92° C. and the amont of water collected was 109.14 grams. In 7 hours, 1039 grams of the syrupy phosphoric acid was added, the temperature was 98° C. Increasing the temperature began and within another 30 minutes, the temperature increase to 108° C. and 270 grams of water was removed during that period. The temperature increased to 160° C. in one hour and 30 minutes and unreacted hexamethyldisiloxane was removed. The total amount of water collected was 297.5 grams. The residue in flask 1 was single phase and clear like water. 2151 grams of residue was obtained. The residue as determined by NMR (nuclear magnetic resonance) was the following mixture: 21.9 weight percent $(Me_3SiO)(OH)_2P=O$, 70.7 weight percent $(Me_3SiO)_2(OH)P=O$, 6.2 weight percent $(Me_3SiO)_3P=O$, and 1.2 weight percent unknown by-product. (Silylphosphate Mixture).

A mixture of 8 weight percent of the Silylphosphate Mixture and 92 weight percent of cyclopolydimethylsiloxane being a mixture of cyclics having from 3 to 7 dimethylsiloxane units per molecule was prepared and allowed to stand for 40 days at room temperature. The resulting siloxanyl-phosphate mixture had the following composition as determined by P-31 and Si-29 NMR;
9.2 weight percent of monosiloxanyl-phosphate of the formula

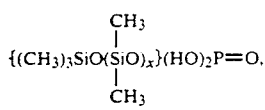

81.6 weight percent of a disiloxanyl-phosphate of the formula

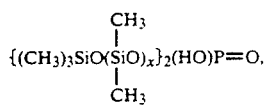

and 9.2 weight percent of a trisiloxanyl-phosphate of the formula

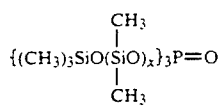

and less than 0.02 weight percent of an unknown material, wherein x has an average value of about 21. This siloxanyl-phosphate mixture is designated herein as Siloxanyl-Phosphate Mixture A.

A mixture of 250 parts of the Silylphosphate Mixture and 490 parts of cyclopolydimethylsiloxane being a mixture of cyclics having from 3 to 7 dimethylsiloxane units per molecule was prepared. The Silylphosphate Mixture was heated to 170° C. and the cyclopolydimethylsiloxane was added over a 35 minute period and then the temperature was increased to 190° C. over a 30 minute period. The resulting siloxanyl-phosphate mixture had the following composition as determined by P-31 and Si-29 NMR;
7.6 weight percent of a monosiloxanyl-phosphate of the formula

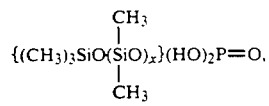

82 weight percent of a disiloxanyl-phosphate of the formula

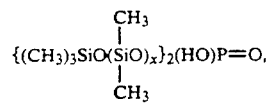

and 9.2 weight percent of a trisiloxanyl-phosphate of the formula

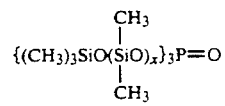

and 0.6 weight percent of an unknown material, wherein x has an average value of about 5. This siloxanyl-phosphate mixture is designated herein as Siloxanyl-phosphate Mixture B.

EXAMPLE 2

A mixture of 3.84 parts of the Silylphosphate mixture as described in Example 1 was mixed with 188.92 parts of cyclopolydimethylsiloxane as described in Example 1 at 24° C. This mixture, one hour after mixing, was used to stabilize potassium ion in a polydimethylsiloxane product of polymerization as described below and is designated Mixture 1. This mixture was maintained at about 25° C. for 16 days. The increasing viscosity of the reacting mixture showed the formation of the siloxanyl-phosphate mixture. This siloxanyl-phosphate mixture was then used to stabilize the potassium ions in a polydimethylsiloxane product of polymerization as described below and is designated as Mixture 2. The viscosity of Mixture 1 was 13.5 centipoise (cp) and the viscosity of Mixture 2 was 79 cp. After 36 days the viscosity of the mixture was 306 cp and was still increasing.

A mixture of 97.89 parts of a mixture of cyclic polydimethylsiloxanes in which the majority of the cyclics have from 3 to 6 dimethylsiloxane units and 2.11 parts of dimethylvinylsiloxy endblocked polydimethylsiloxane having about six dimethylsiloxane units per molecule, was prepared. The resulting mixture was divided into two portions and each was heated to 170° C. and potassium silanolate in an amount to provide 100 ppm potassium were added and then polymerized by heating at 175° C. for 100 minutes (equilibrium was reached within this time). Then carbon dioxide was used to stabilize the potassium ion. After 5 minutes, siloxanyl-phosphate mixture, as described in the Table, was added to further stabilize the catalyst at a molar ratio of K:P of 1.2:1.0. Then 5 minutes later a vacuum was pulled and the temperature was increased to 230° C. After about 35 minutes, the heat was removed and the resulting polymer was allowed to cool. Weight loss after 3 hours at 150° C. on a 5 g sample was determined for each siloxanyl-phosphate stabilized portion. The viscosity was determined by ASTM D 1084 Method B (Brookfield viscometer). The amount of trimethylsiloxy unit available for reaction with the polydiorganosiloxane chain ends was determined by measuring the amount of such units in the overhead after pulling the vacuum. Such trimethylsiloxy unit was available to react with the polydiorganosiloxane ends which causes the ends to become unreactive in compositions made to cure through the vinyl ends. The results of the weight loss, viscosity, and amount of trimethylsiloxy unit were as shown in the Table.

TABLE

| SILOXANYL-PHOSPHATE MIXTURE | VISCOSITY OF POLYMER CP | WEIGHT LOSS % | TRIMETHYL-SILOXY IN OVERHEAD PPM |
|---|---|---|---|
| MIXTURE 1 | 4,850 | 0.83 | 1155 |
| MIXTURE 2 | 4,690 | 0.94 | 422 |

The table shows that the viscosity of the polymer stabilized with the Mixture 1 and Mixture 2 were about the same and the weight loss was about the same. The major difference was the amount of trimethylsiloxy unit in the overhead, almost three times as much in the unreacted (Mixture 1) mixture which contained no dimethylsiloxane units between the trimethylsiloxy unit and the phosphorous atom of the silylphosphate as in the reacted mixture (Mixture 2) which contained siloxanyl-phosphate as defined by this invention. The larger amount of trimethylsiloxy unit, using Mixture 1, would produce about three times the number of unreactive end groups compared to the number of unreactive end groups from Mixture 2.

That which is claimed is:

1. A siloxanyl-phosphate mixture consisting essentially of 5 to 30 weight percent of a monosiloxanyl-phosphate of the formula $$\{(CH_3)_3SiO(SiO)_x\}(HO)_2P=O,$$
with $CH_3$ side groups on the $(SiO)_x$ unit, 70 to 85 weight percent of a disiloxanyl-phosphate of the formula $$\{(CH_3)_3SiO(SiO)_x\}_2(HO)P=O,$$
with $CH_3$ side groups, and 2 to 11 weight percent of a trisiloxanyl-phosphate of the formula $$\{(CH_3)_3SiO(SiO)_x\}_3P=O$$
with $CH_3$ side groups wherein x has an average value of from 3 to 30.

2. A method of making siloxanyl-phosphate mixture consisting essentially of 5 to 30 weight percent of a monosiloxanyl-phosphate of the formula $$\{(CH_3)_3SiO(SiO)_x\}(HO)_2P=O,$$
with $CH_3$ side groups, 70 to 85 weight percent of a disiloxanyl-phosphate of the formula $$\{(CH_3)_3SiO(SiO)_x\}_2(HO)P=O,$$
with $CH_3$ side groups, and 2 to 11 weight percent of a trisiloxanyl-phosphate of the formula $$\{(CH_3)_3SiO(SiO)_x\}_3P=O$$
with $CH_3$ side groups wherein x has an average value of from 3 to 30 comprising mixing cyclopolydimethylsiloxanes having an average of from 3 to 7 dimethylsiloxane units per molecule with a silylphosphate mixture consisting essentially of 10 to 30 weight percent of a monosilyl phosphate of the formula $$\{(CH_3)_3SiO\}(HO)_2P=O,$$

70 to 85 weight percent of a disilyl phosphate of the formula $$\{(CH_3)_3SiO\}_2(HO)P=O,$$

and 2 to 7 weight percent of a trisilyl phosphate of the formula $$\{(CH_3)_3SiO\}_3P=O$$

to form a cyclopolydimethylsiloxane-silylphosphate mixture and reacting the cyclopolydimethylsiloxane-silylphosphate mixture for a time and at a temperature to produce a siloxanyl-phosphate mixture.

3. The method in accordance with claim 2 in which the produced siloxanyl-phosphate mixture is packaged in an moisture tight container for storage.

4. In a method of making polydiorganosiloxane with a basic compound having a metal ion comprising combining cyclic polydiorganosiloxanes and the basic compound and heating to polymerize the cyclic polydiorganosiloxane, thereafter stabilizing the metal ion in the resulting polydiorganosiloxane using a stabilizing material, the improvement consisting essentially of using as the stabilizing material, a siloxanyl-phosphate mixture consisting essentially of 5 to 30 weight percent of a monosiloxanyl-phosphate of the formula $$\{(CH_3)_3SiO(SiO)_x\}(HO)_2P=O,$$
with $CH_3$ side groups, 70 to 85 weight percent of a disiloxanyl-phosphate of the formula $$\{(CH_3)_3SiO(SiO)_x\}_2(HO)P=O,$$
with $CH_3$ side groups, and 2 to 11 weight percent of a trisiloxanyl-phosphate of the formula $$\{(CH_3)_3SiO(SiO)_x\}_3P=O$$
with $CH_3$ side groups wherein x has an average value of from 3 to 30.

5. In a method of making polydiorganosiloxane with a basic compound having a metal ion comprising combining cyclic polydiorganosiloxanes and the basic compound and heating to polymerize the cyclic polydiorganosiloxane, thereafter stabilizing the metal ion in the resulting polydiorganosiloxane using a stabilizing material, the improvement consisting essentially of using as the stabilizing material, a combination of carbon dioxide gas and a siloxanyl-phosphate mixture consisting essentially of 5 to 30 weight percent of a monosiloxanyl-phosphate of the formula $$\{(CH_3)_3SiO(SiO)_x\}(HO)_2P=O,$$
with $CH_3$ side groups, 70 to 85 weight percent of a disiloxanyl-phosphate of the formula
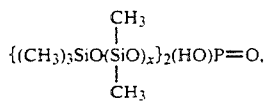
and 2 to 11 weight percent of a trisiloxanyl-phosphate of the formula
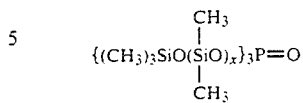
wherein x has an average value of from 3 to 30.
* * * * *